United States Patent [19]

Bouillon et al.

[11] Patent Number: 4,503,033
[45] Date of Patent: Mar. 5, 1985

[54] DITHIOETHER-BASED COSMETIC COMPOSITION FOR THE TREATMENT OF THE OILY STATE OF HAIR AND SKIN

[75] Inventors: Claude Bouillon, Eaubonne; Jean Maignan, Tremblay les Gonesse, both of France

[73] Assignee: Societe Anonyme dite: L'Oreal, Paris, France

[21] Appl. No.: 401,525

[22] Filed: Jul. 26, 1982

Related U.S. Application Data

[62] Division of Ser. No. 53,417, Jun. 29, 1979, Pat. No. 4,348,383.

[30] Foreign Application Priority Data

Jul. 12, 1978 [FR] France ............................... 78 20801

[51] Int. Cl.³ .......................... A61K 7/06; A61K 7/11
[52] U.S. Cl. ............................. 424/47; 424/DIG. 4; 424/70; 424/78; 424/80; 424/81; 549/445; 562/426
[58] Field of Search ............... 424/70, 47, DIG. 4; 562/426; 549/445

[56] References Cited

U.S. PATENT DOCUMENTS

| | | | |
|---|---|---|---|
| 3,225,085 | 12/1965 | Eby ...................................... | 562/426 |
| 3,879,560 | 4/1975 | Kalopissis ............................ | 562/426 |
| 3,968,218 | 7/1976 | Bouillon ....................... | 424/DIG. 4 |
| 4,035,492 | 7/1977 | Kalopissis et al. ............ | 424/DIG. 5 |
| 4,134,879 | 11/1979 | Schmidt ............................... | 562/426 |
| 4,151,301 | 4/1979 | Kalopissis ..................... | 424/DIG. 4 |
| 4,204,064 | 5/1980 | Kalopissis ..................... | 424/DIG. 4 |
| 4,348,383 | 9/1982 | Bouillon et al. ..................... | 424/70 |

FOREIGN PATENT DOCUMENTS 1333754  11/1963  France ................................. 424/59

*Primary Examiner*—Dale R. Ore
*Attorney, Agent, or Firm*—Cushman, Darby & Cushman

[57] ABSTRACT

A cosmetic composition for the treatment of the oily appearance of hair and skin so as to reduce or eliminate said oily appearance comprises in a suitable cosmetic vehicle at least one compound of the formula

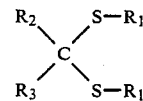

wherein $R_1$ is either

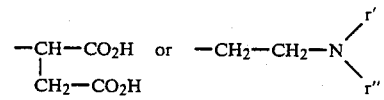

wherein r' and r" can be hydrogen, 2-hydroxy ethyl, 2-hydroxy propyl or 2,3-dihydroxy propyl, $R_2$ is $-CH_3$, $-CO_2H$, $-C_6H_5p\text{-}OCH_3$, $-C_6H_5$,

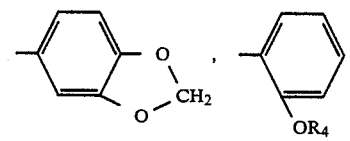

wherein $R_4$ is

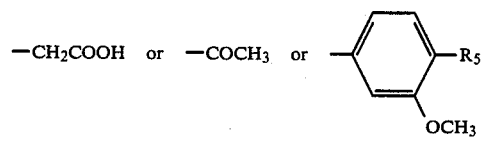

wherein $R_5$ is $-OH$, $-OCH_3$, $-OC_4H_9$ or $-OCH_2COOH$ and $R_3$ is hydrogen or methyl, or $R_2$ and $R_3$ together form

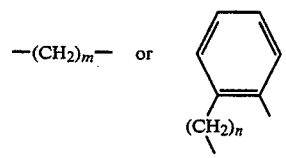

wherein m is 3-5 and n is 2-5.

28 Claims, No Drawings

DITHIOETHER-BASED COSMETIC COMPOSITION FOR THE TREATMENT OF THE OILY STATE OF HAIR AND SKIN

This is a division of application Ser. No. 53,417 filed June 29, 1979, now, U.S. Pat. No. 4,348,383.

The present invention relates to a new cosmetic composition for the treatment of the oily appearance of the hair and skin.

The present invention also relates to new chemical compounds and to a process of producing them.

Background of the Invention

Heretofore in an effort to combat efficiently against the oily state or appearance of the hair and skin, there have been employed compositions containing sulfur derivatives and, principally, thioethers derived from cysteine or cysteamine.

General Description of the Invention

The present invention relates to the use of a new class of sulfur derivatives and, principally, to dithioethers which provide excellent results in the treatment of the oily appearance of the hair and skin by significantly reducing or eliminating this oily and unaesthetic appearance.

Thus, the present invention relates to a cosmetic composition for the treatment of the oily appearance of the hair and skin, said composition containing in combination in a suitable cosmetic vehicle or carrier, at least one active compound of the formula:

$$\begin{array}{c} R_2 \\ \phantom{R}\diagdown \\ \phantom{R_3}C \\ \phantom{R}\diagup \\ R_3 \end{array} \begin{array}{c} S-R_1 \\ \phantom{X} \\ \phantom{X} \\ S-R_1 \end{array} \quad (I)$$

wherein
$R_1$ represents either $$-\underset{\underset{CH_2-CO_2H}{|}}{CH}-CO_2H \quad \text{or} \quad -CH_2-CH_2-N\diagup\begin{array}{c}r'\\\diagdown r''\end{array}$$

wherein $r'$ and $r''$ each independently represent hydrogen, 2-hydroxy ethyl, 2-hydroxy propyl or 2,3-dihydroxy propyl, $R_2$ represents a member selected from the group consisting of
- (i) $-CH_3$,
- (ii) $-CO_2H$,
- (iii) $-C_6H_5p-OCH_3$,
- (iv) $-C_6H_5$, (v) a phenyl ring substituted with $-O-CH_2-O-$ (methylenedioxy)

(vi) a phenyl ring substituted with $-OR_4$ wherein $R_4$ represents $-CH_2COOH$ or $-COCH_3$, and (vii) a phenyl ring substituted with $-R_5$ and $-OCH_3$ wherein $R_5$ represents $-OH$, $-OCH_3$, $-OC_4H_9$ or $-OCH_2COOH$, and $R_3$ represents either hydrogen or methyl, or $R_2$ and $R_3$ together form a divalent radical of the formula $$-(CH_2)_m- \quad \text{or} \quad \begin{array}{c}\text{(phenyl ring with)}\\(CH_2)_n\end{array}$$

wherein m is 3–5 inclusive and n is 2–5 inclusive.

When in formula I, above, $R_1$ represents $$-CH_2-CH_2-N\diagup\begin{array}{c}r'\\\diagdown r''\end{array},$$

the active compound can be provided in the form of a salt obtained with the aid of a mineral or organic acid, such as for example, hydrochloric acid, malic acid, tartaric acid, camphosulfonic acid and the like.

Also, when in formula I, $R_1$ represents $$-\underset{\underset{CH_2-COOH}{|}}{CH}-COOH,$$

the active compounds can be provided in the form of mono- or di-salts obtained with the aid of a mineral base such as for example an alkali or alkaline earth hydroxide (sodium, potassium and the like) or with the aid of an organic amine, such as for example triethanolamine.

Representative active compounds of formula I, useful in the compositions of the present invention, include for instance:
(1) 2,2'-(isopropylidene dithio) diethylamine,
(2) bis-(2-amino ethylthio) acetic acid,
(3) α,α'-(p-methoxy benzylidene dithio) disuccinic acid,
(4) 2,2'-(p-methoxy benzylidene dithio) diethylamine,
(5) α,α'-(benzylidene dithio) disuccinic acid,
(6) α,α'-(piperonylidene dithio) disuccinic acid,
(7) 2,2'-(piperonylidene dithio) diethylamine,
(8) 2,2'-(2-carboxymethyloxy benzylidene dithio) diethylamine,
(9) α,α'-(vanillylidene dithio) disuccinic acid,

(10) 2,2'-(vanillylidene dithio) diethylamine,
(11) α,α'-(veratrylidene dithio) disuccinic acid,
(12) 2,2'-(veratrylidene dithio) diethylamine,
(13) α,α'-(4,butoxy-3methoxy benzylidene dithio) disuccinic acid,
(14) 2,2'-(4-butoxy-3-methoxy benzylidene dithio) diethylamine,
(15) α,α'-(4-carboxymethyloxy-3-methoxy benzylidene dithio) discuccinic acid,
(16) 2,2'-(4-carboxymethyloxy-3-methoxy benzylidene dithio) diethylamine,
(17) 2,2'-(cyclohexylidene dithio) diethylamine,
(18) 2,2'-(1-carboxy ethylidene dithio) diethylamine,
(19) 2,2'-(1-phenyl ethylidene dithio) diethylamine,
(20) 2,2'-(2-acetoxy benzylidene diothio) diethylamine, and the salts thereof.

The cosmetic compositions in accordance with the present invention contain at least one active compound of formula I above, or at least one of their salts, in suspension or in solution in water, an alcohol (such as ethanol or isopropanol), in a hydroalcoholic solution, in an oil, in an emulsion, or in a gel.

The concentration of the active compound of the present invention is generally between 0.1 and 20 percent, and preferably between 1 and 10 percent, by weight based on the total weight of said composition.

The capillary compositions of the present invention can contain the active compounds of formula I, either singly, or as an admixture of two or more of them, or even in admixture with other compounds with are known to be useful in combatting the oily and unaesthetic appearance of the hair.

The capillary compositions of the present invention can also contain other components such as penetrating agents or perfumes, which are generally employed in cosmetic compositions.

The cosmetic compositions of the present invention can be provided as a dry shampoo in the form of a powder or aerosol, not containing a surface active agent. These compositions can usefully be applied to dry hair. In the use of such compositions, the same is applied to dry hair and is permitted to remain thereon for a sufficient period of time, after which the hair is then simply brushed.

The composition of the present invention can also be provided in the form of hair setting lacquers or lotions containing at least one active compound, as defined above, in combination, in a suitable cosmetic vehicle, with at least one conventional cosmetic resin.

Representative useful cosmetic resins include, for instance, polyvinylpyrrolidone; copolymers of polyvinylpyrrolidone and vinyl acetate; copolymers of vinyl acetate and an unsaturated carboxylic acid such as crotonic acid; copolymers resulting from the polymerization of vinyl acetate, crotonic acid and an acrylic or methacrylic ester; copolymers resulting from the copolymerization of vinyl acetate and an alkyl vinyl ether; and copolymers resulting from the copolymerization of vinyl acetate, crotonic acid and a vinyl ester of a long carbon chain acid or even an allyl or methallyl ester of a long carbon chain acid.

The cosmetic resins contained in these hair setting lacquer or lotion compositions can also be colored polymers, that is, polymers containing in the macromolecular chain thereof dye molecules which impart to the hair a particular coloration or shade.

These hair setting lacquer or lotion compositions can also contain direct dyes so as to produce a desired coloration or shade to the hair. They can also contain components which are conventionally employed in cosmetic compositions for fixing the hair in a particular state, such as penetrating agents, cationic compounds, quaternary ammonium salts, vitamins, proteins, more or less hydrolyzed peptides, cellulose or starch derivatives, surface active agents, dyes, perfumes and the like.

Useful cosmetic vehicles include those conventionally employed for the production of hair setting lacquers and lotions or even hair styling compositions.

Thus, these cosmetic compositions can employ as the cosmetic vehicle an alcohol or a hydroalcoholic solution and when a cosmetic resin is present, they provide a hair setting lotion.

The alcoholic or hydroalcoholic solution of the active compound can also be admixed with a suitable amount of liquified propellant gas under pressure and be packaged in an aerosol container to thereby provide a hair setting lacquer.

In these hair setting lotions or lacquers, the concentration of the active compound is generally between 0.1 and 10 weight percent, but preferably, between 1 and 3 weight percent, based on the total weight of said composition while the concentration of the resin is between, preferably, 0.1 and 10 weight percent of said total composition.

The cosmetic compositions of the present invention can also be provided in the form of a treating shampoo having the appearance of a liquid which can be clear, opaque or pearly, or having the appearance of a cream or a gel. These shampoo compositions are also effective in significantly reducing or eliminating an oily and unaesthetic appearance of the hair.

These shampoo compositions are essentially characterized by the fact that they contain, in combination, at least one anionic, cationic, nonionic or amphoteric detergent with at least one active compound of formula I.

Representative anionic detergents include, for instance, alkyl sulfates, alkyl ether sulfates, alkyl polyether sulfates, alkyl sulfonates (the alkyl groups having from 8 to 18 carbon atoms), sulfated monoglycerides, sulfoned monoglycerides, sulfated alkanolamides, sulfoned alkanolamides, soaps of fatty acids, monosulfosuccinates of fatty alcohols, condensation products of fatty acids with isethionic acid, condensation products of fatty acids with methyl taurine, condensation products of fatty acids with sarcosine, condensation products of fatty acids with protein hydrolyzate.

Representative cationic detergents include, for instance, long chain quaternary ammoniums, esters of fatty acids and amino alcohols and polyetheramines.

Representative non-ionic detergents include, for instance, esters of polyols and sugars, condensation product of ethylene oxide on fatty acids, on fatty alcohols, on long chain alkylphenols, on long chain mercaptans, on long chain amides and polyethers of polyhydroxylated fatty alcohols.

Representative amphoteric detergents include, for instance, asparagine, condensation products of monochloroacetic acid on imidazolines, alkyl amino propionates, betain derivatives or amine oxides.

These shampoo compositions contain generally from 0.1% to 15%, but preferably, from 1 to 10% by weight of the active compound based on the total weight of the composition. They also contain for example from 4 to 20%, but preferably, from 5 to 10% by weight of detergents in solution in an aqueous medium.

The shampoos such as defined above can also contain conventional cosmetic components such as perfumes and dyes. They can also contain thickening agents such as alkanolamides of fatty acids, cationic polymers such as the copolymers of quaternized vinylpyrrolidone, cationic cellulose polymers, cellulose derivatives such as carboxymethyl or hydroxymethyl cellulose, esters of long chain polyols, and natural gums, whereby the composition can be provided in the form of a cream or gel.

Additionally, these shampoos can be provided in the form of powders which can either be applied to wet hair, or can be solubilized in a suitable volume of water before washing the hair.

These shampoo compositions can also include dyes and thus be employed to color the hair.

Generally, satisfactory results can be obtained by a weekly application of the shampoo, which results in a significant reduction and, in certain cases, essentially complete elimination of the oily appearance of the hair, while at the same time providing normal care of the hair.

The present invention also relates to a composition containing the active compound, as defined above, together with a suitable skin-compatible cosmetically acceptable vehicle, which composition can be applied to the skin to improve its appearance.

Such skin-applicable, or topically applicable compositions can be provided preferably in the form of creams, milks, gels, dermatological cakes or aerosol foams. These compositions can also be provided in the form of aqueous or hydroalcoholic lotions. They contain generally from 0.1 to 15% by weight, based on the total weight of the composition, of the active compound defined above. Preferably from 1 to 5% by weight of the active compound is employed.

The present invention also relates to a new compound having the formula:

$$\begin{array}{c} R_2 \\ \diagdown \\ \phantom{R_2}C \\ \diagup \\ R_3 \end{array} \begin{array}{c} S-R_1 \\ \\ S-R_1 \end{array} \quad (II)$$

wherein
$R_1$ represents either $$\begin{array}{c} -CH-CO_2H \\ | \\ CH_2-CO_2H \end{array} \text{ or } -CH_2-CH_2-N\begin{array}{c} r' \\ \diagdown \\ r'' \end{array},$$

wherein r' and r'' each independently represent hydrogen, 2-hydroxyethyl, 2-hydroxy propyl or 2,3-dihydroxy propyl, $R_2$ represents a member selected from the group consisting of
(i) —$CH_3$ and $R_3$ is hydrogen,
(ii) —$CO_2H$
(iii) —$C_6H_5$p—$OCH_3$,
(iv) —$C_6H_5$ and $R_3$ represents methyl for values (ii)–(iv).

(v) phenyl-methylenedioxy ring system with $OCH_2O$ (vi) phenyl with $OR_4$ wherein $R_4$ represents —$CH_2COOH$ or —$COCH_3$, and (vii) phenyl with $R_5$ and $OCH_3$ wherein $R_5$ represents —OH, —$OCH_3$, —$OC_4H_9$ or —$OCH_2COOH$, and $R_3$ represents hydrogen or methyl for values (v)–(vii), immediately above, or $R_2$ and $R_3$ taken together, form a divalent radical of the formula $$-(CH_2)_m- \quad \text{or} \quad \text{(benzo-fused ring with }(CH_2)_n)$$

wherein m is 3–5 inclusive and n is 2–5 inclusive, and the salts thereof.

Compounds of formula II, above, wherein $R_1$ is $$-CH_2-CH_2-N\begin{array}{c} r' \\ \diagdown \\ r'' \end{array}$$

can be provided in the form of a salt with the aid of a mineral or organic acid. Compounds of formula II, above, wherein $R_1$ is $$\begin{array}{c} -CH-COOH \\ | \\ CH_2-COOH \end{array}$$

can be provided in the form of a mono- or di-salt obtained with the aid of a mineral or organic base.

Representative compounds of formula II include:
α,α'-(piperonylidene dithio) disuccinic acid,
2,2'-(piperonylidene dithio) diethylamine,
2,2'-(2-carboxymethyloxy benzylidene dithio) diethylamine,
α,α'-(vanillylidene dithio) disuccinic acid,
2,2'-(vanillylidene dithio) diethylamine,
α,α'-(veratrylidene dithio) disuccinic acid,
2,2'-(veratrylidene dithio) diethylamine, α,α'-(4-butoxy-3-methoxy benzylidene dithio) disuccinic acid, 2,2'-(4-butoxy-3-methoxy benzylidene dithio) diethylamine, α,α'(4-carboxymethyl-3-methoxy benzylidene dithio) disuccinic acid, 2,2'-(4-carboxymethyloxy-3-methoxy benzylidene dithio) diethylamine, 2,2'-(cyclohexylidene dithio) diethylamine, 2,2'-(1-carboxy ethylidene dithio) diethylamine, 2,2'-(1-phenyl ethylidene dithio) diethylamine, 2,2'-(2-acetoxy benzylidene dithio) diethylamine, and the salts of these said compounds.

The present invention also relates to process for preparing the active compounds such as defined above.

This process can be represented by the following reaction scheme:

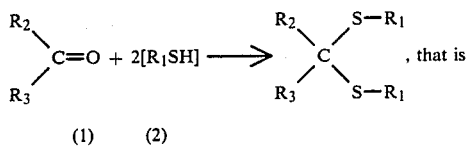

(1)    (2)

that is a carbonyl compound (1) is reacted with at least two equivalents of a thiod (2).

The reaction preferably is carried out in a solvent medium and in the presence of an acid catalyst.

The solvent, preferably, is an organic acid (such as formic acid or acetic acid), an alcohol, dioxane or a mixture of these particular solvents.

The acid catalyst is preferably a strong mineral acid or a Lewis acid such as for example zinc chloride or boron trifluoride.

However, when the solvent is an organic acid, (principally, formic acid), the reaction is carried out in the absence of a catalyst.

The reaction temperature is generally between 0° and 100° C. and the reaction time between 1 and 48 hours.

The following non-limiting Examples illustrate the invention.

Examples of Preparation

Example 1 α-α'-(p-methoxybenzylidene dithio) disuccinic acid (Compound 3)

A mixture of 54.4 g (0.4 mole) of anisic aldehyde and 120 g (0.8 mole) of α-mercapto succinic acid in 1 liter of formic acid is stirred for two hours under a nitrogen atmosphere. The reaction mixture is permitted to stand for 24 hours at which time it is then concentrated under reduced pressure. The residue is taken up and crystallized in a mixture of water and ethanol. After filtering and drying 136 g of white crystals having a melting point of 255° C. are obtained.

Analysis: $C_{16}H_{18}O_9S_2$: Calc %: C 45.93; H 4.33; S 15.33. Theory %: C 45.73; H 4.34; S 15.18.

Example 2 2,2'-(2-carboxymethyloxy benzylidene dithio) diethylamine (dihydrochloride) (Compound 8)

For a period of two hours a stream of dry gaseous HCl is bubbled into a mixture of 90 g (0.5 mole) of o-formyl phenoxyacetic acid and 115 g (1 mole) of β-mercaptoethylamine hydrochloride in 1 liter of acetic acid, previously de-aerated by passage therethrough of nitrogen. The reaction mixture is then heated at 60° C., after which it is permitted to stand for 24 hours at ambient temperature. The resulting crystallized product is filtered off and the filtrate is concentrated to dryness, with the resulting residues being recrystallized in a mixture of ethanol and methanol. 156 g of white crystals melting at 225° C. are thus recovered.

Analysis: $C_{13}H_{22}Cl_2N_2O_3S_2$: Calc %: S 16.47; N 7.19. Theory %: S 16.24; N 7.04.

Example 3 α,α'-(veratrylidene dithio) disuccinic acid (compound 11)

There is heated in acetic acid (300 ml) for two hours at 65° C., with stirring, a mixture of 16.6 g of veratric aldehyde and 30 g of α-mercaptosuccinic acid, in the presence of a small amount of boron trifluoride, in the form of an acetic complex. After 12 hours of rest, the reaction mixture is concentrated under reduced pressure and the solid obtained is crystallized in a mixture of benzene and ethyl acetate. After filtering and drying, 31 g of white crystals melting at 187° C. are recovered.

Analysis: $C_{17}H_{20}O_{10}S_2$: Calc %: C 45.53; H 4.50; S 14.30. Theory %: C 45.24; H 4.74; S 14.38.

Under the same conditions as those described above, the compounds listed in Table I below have been prepared.

TABLE 1

| Compound No. | Initial Reactants Thiol | Carbonyl Compound | Solvent | Initial Temp. °C. | Yield % | Melting Point °C. | Elemental Analysis C | H | Calc % Theory % N | S |
|---|---|---|---|---|---|---|---|---|---|---|
| 1 | a | Acetone | Ethanol | 0° C. | 80 | 215° | | | 10.50 | 24.00 |
| | | | | | | | | | 10.51 | 24.31 |
| 2 | a | Glyoxylic acid | Acetic acid + dioxan | 20° | 65 | 180° | | | 9.89 | 22.64 |
| | | | | | | | | | 9.68 | 22.71 |
| 4 | a | Anisaldehyde | Ethanol | 0° | 70 | 217° | | | 8.11 | 18.60 |
| | | | | | | | | | 8.12 | 18.32 |
| 7 | a | Piperonal | Ethanol | 50° | 80 | 207° | | | 7.79 | 17.84 |
| | | | | | | | | | 7.61 | 17.93 |
| 9 | b | Vanillin | Acetic acid | 20° | 72 | 225° | 44.23 | 4.18 | | 14.76 |
| | | | | | | | 44.33 | 4.12 | | 14.60 |
| 10 | a | Vanillin | Ethanol | 0° | 55 | 194° | | | 7.75 | 17.75 |
| | | | | | | | | | 7.54 | 17.79 |
| 12 | a | Veratric aldehyde | Ethanol | 50° | 75 | 169° | | | 7.46 | 17.08 |
| | | | | | | | | | 7.25 | 16.94 |
| 13 | b | o-butyl vanillin | Acetic acid | 60° | 50 | 188° | 48.96 | 5.34 | | 13.07 |
| | | | | | | | 49.01 | 5.42 | | 13.04 |
| 14 | a | o-butyl vanillin | Ethanol | 50° | 65 | 212° | 46.03 | 7.24 | | 15.36 |
| | | | | | | | 45.71 | 7.34 | | 15.49 |
| 15 | b | o-carboxymethyl vanillin | Acetic acid | 60° | 45 | 152° | 43.89 | 4.09 | | 13.02 |
| | | | | | | | 43.70 | 4.30 | | 13.00 |

TABLE 1-continued

| Compound No. | Initial Reactants Thiol | Initial Reactants Carbonyl Compound | Solvent | Initial Temp. °C. | Yield % | Melting Point °C. | Elemental Analysis C | Elemental Analysis H | Calc % Theory % N | Calc % Theory % S |
|---|---|---|---|---|---|---|---|---|---|---|
| 16 | a | o-carboxymethyl vanillin | Acetic acid | 60° | 65 | 114° | 38.44 38.60 | 5.91 6.30 | 6.40 6.55 | |
| 17 | a | Cyclohexanone | Ethanol | 50° | 80 | 207° | | | 9.11 8.97 | 20.86 20.85 |
| 18 | a | Pyruvic acid | Acetic acid | 50° | 75 | 220° | | | 9.42 9.18 | 21.57 21.87 |
| 19 | a | Acetophenone | Ethanol | 80° | 50 | 194° | | | 8.50 8.33 | 19.47 19.64 |
| 20 | a | o-acetyl salicyl aldehyde | Acetic acid | 50° | 85 | 190° | | | 7.50 7.57 | 17.17 17.11 | a = β-mercaptoethylamine hydrochloride
b = α-mercaptosuccinic acid

Examples of Compositions

Example A-Capillary lotion for oily hair

This capillary lotion is used, after shampooing, on wet hair and before setting the hair.

| | |
|---|---|
| 2,2'-(isopropylidene dithio) diethylamine dihydrochloride (Compound No. 1) | 1 g |
| Vinylacetate/N—vinylpyrrolidone copolymer | 1.5 g |
| Perfume | 0.1 g |
| Ethyl alcohol at 25%, sufficient for | 100 g |

Example B-Milk for oily skin

| | |
|---|---|
| α,α'-(p-methoxybenzylidene dithio) disuccinic acid (Compound No. 3) | 2.8 g |
| Triethanolamine, sufficient for pH = 8 | |
| Crosslinked polyacrylic acid, sold under the trade name "CARBOPOL 934" | 0.375 g |
| Isopropyl ester of the fatty acid of lanolin | 1 g |
| Lanolin oxyethylenated with 5-20 moles of ethylene oxide | 2.5 g |
| Cetylstearyl alcohol oxyethylenated with 25 moles of ethylene oxide | 3 g |
| Lauric diethanolamide | 2 g |
| Methyl p-hydroxybenzoate | 0.1 g |
| Propyl p-hydroxybenzoate | 0.1 g |
| Water, sufficient for | 100 g |

Example C-Capillary lotion for oily hair

| | |
|---|---|
| α,α'-(vanillylidene dithio) disuccinic acid (Compound No. 9) | 0.4 g |
| Potassium hydroxide, sufficient for pH = 4.5 | |
| Calcium pantothenate | 0.5 g |
| Perfume | 0.1 g |
| Ethyl alcohol (40%), sufficient for | 100 g |

Example D-Treating lotion for the skin

| | |
|---|---|
| 2,2'-(cyclohexylidene dithio) diethylamine, dihydrochloride (Compound No. 17) | 1.5 g |
| Cetyldimethylbenzyl ammonium chloride | 0.2 g |
| Ethylalcohol | 13 ml |
| Polyethylene glycol | 10 g |
| Perfume | 0.1 g |
| Soluble dyes | 0.1 g |
| Sterile demineralized water, sufficient for | 100 g |

Example E-Clear liquid shampoo

| | |
|---|---|
| 2,2'-(piperonylidene dithio) diethylamine, dihydrochloride (Compound No. 7) | 2 g |
| Lauryl alcohol polyoxyethylenated with 12 moles of ethylene oxide | 13 g |
| Copra diethanolamide | 4 g |
| Copolymer of quaternized polyvinyl pyrrolidone, sold under the trade name GAFQUAT 755 | 0.4 g |
| Perfume | 0.2 g |
| Water, sufficient for | 100 g |

Example F-Cream for oily skin

| | |
|---|---|
| 2,2'-(2-acetoxy benzylidene dithio) diethylamine, dihydrochloride (Compound No. 20) | 1.5 g |
| Cetylstearyl alcohol | 2 g |
| Glycerol monostearate | 4 g |
| Cetyl alcohol | 4 g |
| Isopropyl palmitate | 8 g |
| Stearate polyoxyethylenated with 20 moles of ethylene oxide | 6 g |
| Calophyllum oil | 1 g |
| Propyl p-hydroxy benzoate | 0.3 g |
| Tetradecyltrimethyl ammonium bromide | 0.3 g |
| Sterile, demineralized water, sufficient for | 100 g |

Example G-Shampoo powder

| | |
|---|---|
| Potassium salt of α,α'-(4-butoxy-3-methoxy benzylidene dithio) disuccinic acid (Compound No. 13) | 12 g |
| Sodium lauryl sulfate | 40 g |
| Condensation products of the fatty acids of copra on sodium isethionate, sold under the trade name "HOSTAPON K.A." | 39 g |

Example H-Dermatological cake

| | |
|---|---|
| Bis-(2-amino ethylthio) acetic acid | 2.5 g |
| Sodium alkane sulfonate, sold under | 80 g |

-continued

| the trade name "IGEPON A" | |
|---|---|
| Liquid lanolin | 12 g |
| Purcellin oil | 2 g |
| Chlorhexidine | 0.5 g |
| Titanium dioxide | 2 g |
| Perfume | 2.5 g |

Example I-Milk for oily skin

| | |
|---|---|
| α,α'-(4-carboxymethyloxy-3-methoxy benzylidene dithio) disuccinic acid | 1.6 g |
| Triethanolamine, sufficient for pH = 8 | |
| Crosslinked polyacrylic acid, sold under the trade name "CARBOPOL 934" | 0.375 g |
| Isopropyl ester of the fatty acids of lanolin | 1 g |
| Lanolin oxyethylenated with 5-20 moles of ethylene oxide | 2.5 g |
| Cetylstearyl alcohol oxyethylenated with 25 moles of ethylene oxide | 3 g |
| Lauric diethanolamide | 2 g |
| Methyl p-hydroxy benzoate | 0.1 g |
| Propyl p-hydroxy benzoate | 0.1 g |
| Water, sufficient for | 100 g |

Example J-Lotion for daily use for the care of oily hair

| | |
|---|---|
| 2,2'-(piperonylidene dithio) diethanolamine, dihydrochloride | 0.4 g |
| Pyridoxine camphosulfonate | 0.3 g |
| Perfume | 0.1 g |
| Dye | 0.1 g |
| Ethyl alcohol/water 50%, sufficient for | 100 g |

Example K-Pearly liquid shampoo

| | |
|---|---|
| α,α'-(4-butoxy-3-methoxy benzylidene dithio) disuccinic acid | 6 g |
| Potassium hydroxide, sufficient for pH = 7.5 | |
| Sodium lauryl sulfate oxyethylenated with 2.2 moles of ethylene oxide | 9 g |
| Sodium monolauryl sulfosuccinate | 1 g |
| Polyethylene glycol distearate | 2 g |
| Lauric diethanolamide | 2 g |
| Perfume | 0.3 g |
| Water, sufficient for | 100 g |

Example L-Cream Shampoo

| | |
|---|---|
| 2,2'-(isopropylidene dithio) diethylamine | 3.5 g |
| Lactic acid, sufficient for pH = 6.5 | |
| Sodium lauryl sulfate | 12 g |
| Condensation product of copra fatty acids on methyl taurine, sold under the trade name "HOSTAPON C.T." | 40 g |
| | 40 g |
| Lauric monoethanolamide | 2 g |
| Glycerol monostearate | 4 g |
| Perfume | 0.2 g |
| Water, sufficient for | 100 g |

Example M-Cream for oily hair

| | |
|---|---|
| α,α'-(vanillylidene dithio) disuccinic acid | 1.8 g |
| Triethanolamine, sufficient for pH = 6.5 | |
| Stearate polyoxyethylenated, sold under the trade name "Myr 49" | 3 g |
| Glycerol monostearate | 4 g |
| Cetyl alcohol | 7 g |
| Vaseline (petrolatum) oil | 8 g |
| Isopropyl myristate | 5 g |
| Methyl p-hydroxy benzoate | 0.3 g |
| Crosslinked polyacrylic acid, 1% solution, sold under the trade name "CARBOPOL 941" | 40 g |
| Water, sufficient for | 100 g |

This cream is applied to the scalp after a shampoo. One massages lightly then leaves to rest about 15 minutes and then one rinses.

Example N-Clear Liquid shampoo

| | |
|---|---|
| α,α'-(4-butoxy-3-methoxy benzylidene dithio) disuccinic acid | 1.5 g |
| Lauryl alcohol polyglycerolated with 4 moles of glycerol | 15 g |
| Copolymer of quaternized N-vinyl-pyrrolidone, sold under the trade name "GAFQUAT 755" | 0.4 g |
| Alkylamine polyethoxylated, sold under the trade name "ETHOMEEN 18/15" | 0.8 g |
| Perfume | 0.1 g |
| Water, sufficient for | 100 g |

Example O-Lotion for oily skin

| | |
|---|---|
| α-α'-(vanillylidene dithio) disuccinic acid | 1.4 g |
| Salicylic acid | 0.2 g |
| Di-isobutyl cresoxyethoxyethyl dimethylbenzylammonium chloride | 0.3 g |
| Polyethyleneglycol tertio-dodecyl thioether | 0.1 g |
| Hydroxyethyl carboxymethyl 2-alkyl imidazolinium, sold under the trade name "MIRANOL C 2 M" | 10 g |
| Perfume | 0.8 g |
| Sterile, demineralized water, sufficient for | 100 g |

Example P-Facial lotion

| | |
|---|---|
| α,α'-(p-methoxy benzylidene dithio) disuccinic acid | 0.8 g |
| Triethanolamine, sufficient for pH = 4.5 | |
| Ethyl alcohol | 16 g |
| Methyl p-hydroxybenzoate | 0.1 g |
| Propyl p-hydroxybenzoate | 0.1 g |
| Perfume | 0.8 g |
| Dye | 0.2 g |
| Water, sufficient for | 100 g |

Example Q-Cream for oily skin

| | |
|---|---|
| 2,2'-(isopropylidene dithio) diethyl ammonium dicampho- | 1.2 g |

-continued

| | |
|---|---|
| sulfonate | |
| Sipol wax (Cire de Sipol) | 5 g |
| Glycerol monostearate | 2 g |
| Hydrogenated polyisobutylene | 3 g |
| Vaseline (petrolatum) oil | 3 g |
| Cetyl alcohol | 1 g |
| Isopropyl ester of the fatty acids of lanolin | 3.5 g |
| Methyl p-hydroxybenzoate | 0.3 g |
| Water, sufficient for | 100 g |

Example R-Lotion for oily skin

| | |
|---|---|
| α,α'-(4-carboxymethyloxy-3-methoxy benzylidene dithio) disuccinic acid | 2 g |
| Triethanolamine, sufficient for pH = 5 | |
| Ethyldiethylene glycol | 10 g |
| Ethanol | 9 g |
| Butylhydroxyanisole | 0.05 g |
| Butylhydroxytoluene | 0.05 g |
| Octyl gallate | 0.0125 g |
| Perfume | 0.5 g |
| Water, sufficient for | 100 g |

What is claimed is:

1. A cosmetic composition for the treatment of the oily appearance of the hair and skin comprising in combination, a suitable cosmetic vehicle and an effective amount of at least one active compound having the formula

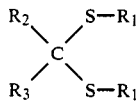

wherein $R_1$ represents

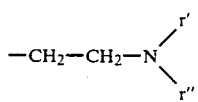

wherein r' and r" each independently represent hydrogen, 2-hydroxyethyl, 2-hydroxypropyl or 2,3-dihydroxypropyl, $R_2$ represents a member selected from the group consisting of
 (i) —CH₃,
 (ii) —CO₂H,
 (iii) —C₆H₅p—OCH₃,
 (iv) —C₆H₅,

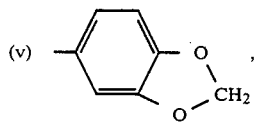

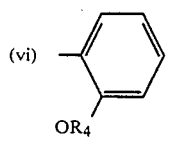

wherein $R_4$ represents —CH₂COOH or —COCH₃ and

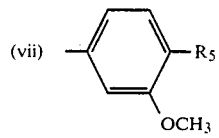

wherein $R_5$ represents —OH, —OCH₃, —OC₄H₉ or —OCH₂COOH, and $R_3$ represents hydrogen or methyl, or $R_2$ and $R_3$ together form a divalent radical of the formula —(CH₂)$_m$—, or of the formula

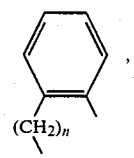

wherein m is 3-5 inclusive and n is 2-5 inclusive and the salts thereof.

2. The composition of claim 1 wherein said active compound is provided in the form of a salt of a mineral or organic acid.

3. The composition of claim 1 wherein said active compound is selected from the group consisting of
 (1) 2,2'-(isopropylidene dithio)diethylamine,
 (2) bis-(2-amino ethylthio) acetic acid,
 (3) 2,2'-(p-methoxybenzylidene dithio)diethylamine,
 (4) 2,2'-(piperonylidene dithio)diethylamine,
 (5) 2,2'-(2-carboxymethyloxybenzylidene dithio) diethylamine,
 (6) 2,2'-(vanillylidene dithio)diethylamine,
 (7) 2,2'-(veratrylidene dithio)diethylamine,
 (8) 2,2'-(4-butoxy-3-methoxy benzylidene dithio) diethylamine,
 (9) 2,2'-(4-carboxymethyloxy-3-methoxy benzylidene dithio)diethylamine,
 (10) 2,2'-(cyclohexylidene dithio)diethylamine,
 (11) 2,2'-(1-carboxyethylidene dithio)diethylamine,
 (12) 2,2'-(1-phenyl ethylidene dithio)diethylamine,
 (13) 2,2'-(2-acetoxy benzylidene dithio)diethylamine, and the salts thereof.

4. The cosmetic composition of claim 1 wherein $R_2$ represents a member selected from the group consisting of
 (i) —C₆H₅p—OCH₃,
 (ii) —C₆H₅,

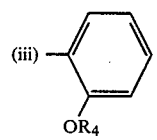

wherein $R_4$ represents —CH₂COOH or —COCH₃, and

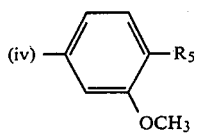

wherein R₅ represents —OH, —OCH₃, —OC₄H₉ or —OCH₂COOH, and
R₃ represents hydrogen or methyl, or R₂ and R₃ together form a divalent radical of the formula

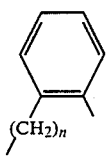

wherein n is 2–5 inclusive.

5. The cosmetic composition of claim 4 wherein the active compound is selected from the group consisting of
(1) 2,2'-(p-methoxy benzylidene dithio)diethylamine,
(2) 2,2'-(2-carboxymethyloxy benzylidene dithio) diethylamine,
(3) 2,2'-(vanillylidene dithio)diethylamine,
(4) 2,2'-(veratrylidene dithio)diethylamine,
(5) 2,2'-(4-butoxy-3-methoxy benzylidene dithio) diethylamine,
(6) 2,2'-(4-carboxymethyloxy-3-methoxy benzylidene dithio)diethylamine,
(7) 2,2'-(1-phenyl ethylidene dithio)diethylamine,
(8) 2,2'-(2-acetoxy benzylidene dithio)diethylamine, and the salts thereof.

6. The composition of claim 1 wherein said active compound is present in an amount between 0.1 and 20 percent by weight based on the total weight of said composition.

7. The composition of claim 1 wherein said active compound is present in an amount between 1 to 10 percent by weight based on the total weight of said composition.

8. The composition of claim 1 wherein said cosmetic vehicle is water, an alcohol, a hydroalcoholic solution, an oil, an emulsion or a gel and said composition constitutes a capillary composition for the care of the scalp.

9. The composition of claim 1 wherein said cosmetic vehicle is an alcoholic or hydroalcoholic solution in combination with an effective amount of a cosmetic resin.

10. The composition of claim 9 wherein said cosmetic resin is selected from the group consisting of polyvinylpyrrolidone, copolymer or polyvinylpyrrolidone and vinyl acetate, copolymer of vinylacetate and an unsaturated carboxylic acid, copolymer resulting from the polymerization of vinyl acetate, crotonic acid and an acrylic or methyacrylic ester, copolymer resulting from the polymerization of vinyl acetate, crotonic acid and alkyl vinyl ether and copolymer resulting from the polymerization of vinyl acetate, crotonic acid and an allyl or methallyl ester of a long carbon chain acid.

11. The composition of claim 9 which also includes a liquified gaseous propellant under pressure and constitutes an aerosol lacquer.

12. The composition of claim 9 wherein said active compound is present in an amount of 0.1 to 10 weight percent thereof and said cosmetic resin is present in an amount of 0.1 to 10 weight percent thereof.

13. The composition of claim 12 wherein said active compound is present in an amount of 1 to 3 weight percent thereof.

14. The composition of claim 1 wherein said active compound is present in an amount of 0.1 to 15 weight percent thereof and said composition also includes an effective amount of at least one of an anionic, cationic, nonionic or amphoteric detergent and constitutes a shampoo composition.

15. The composition of claim 14 wherein said active compound is present in an amount of 1 to 10 weight percent thereof.

16. The composition of claim 14 wherein said detergent is present in an amount of 4 to 20 weight percent thereof.

17. The composition of claim 14 wherein said detergent is present in an amount of 5 to 10 weight percent thereof.

18. The composition of claim 1 for improving the appearance of the skin wherein said active compound is present in an amount of 0.1 to 15 weight percent thereof and said cosmetic vehicle is a skin-compatible cosmetically acceptable vehicle.

19. The composition of claim 18 wherein said active compound is present in an amount of 1 to 5 weight percent thereof.

20. A compound of the formula

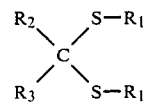

wherein
R₁ represents

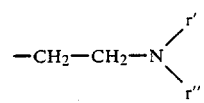

wherein r' and r" each independently represent hydrogen, 2-hydroxyethyl, 2-hydroxypropyl or 2,3-dihydroxypropyl,
R₂ represents a number selected from the group consisting of
(i) —CH₃ and R₃ represents hydrogen,
(ii) —CO₂H,
(iii) —C₆H₅ p—OCH₃,
(iv) —C₆H₅ and R₃ represents methyl for values (ii–iv),

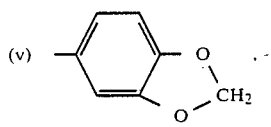

-continued (vi) 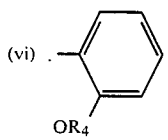

wherein R₄ represents —CH₂COOH or —COCH₃, (vii) 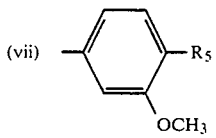

wherein R₅ represents —OH, —OCH₃, —OC₄H₉ or —OCH₂COOH, and R₃ represents hydrogen or methyl for values (v)–(vii), or R₂ and R₃ together form a divalent radical of the formula —(CH₂)$_m$— or 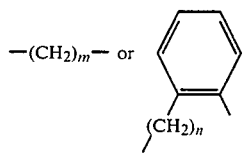

wherein m is 3–5 inclusive and n is 2–5 inclusive, and the salts thereof.

21. The compound of claim 20 selected from the group consisting of
(1) 2,2'-(piperonylidene dithio)diethylamine,
(2) 2,2'-(2-carboxymethyloxybenzylidene dithio) diethylamine,
(3) 2,2'-(vanillylidene dithio)diethylamine,
(4) 2,2'-(veratrylidene dithio)diethylamine,
(5) 2,2'-(4-butoxy-3-methoxy benzylidene dithio) diethylamine,
(6) 2,2'-(4-carboxymethyloxy-3-methoxy benzylidene dithio)diethylamine,
(7) 2,2'-(cyclohexylidene dithio)diethylamine,
(8) 2,2'-(1-carboxy ethylidene dithio)diethylamine,
(9) 2,2'-(1-phenyl ethylidene dithio)diethylamine,
(10) 2,2'-(2-acetoxy benzylidene dithio)diethylamine, and the salts thereof.

22. A process for improving the appearance of oily skin or hair so as to reduce or eliminate said oily appearance comprising applying to said oily appearing skin or hair an effective amount of the composition of claim 1.

23. A cosmetic composition for the treatment of the oily appearance of the hair comprising in combination, in an alcoholic or hydroalcoholic solution, (1) an effective amount of at least one active compound having the formula

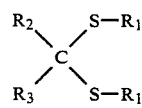

wherein
R₁ represents

—CH—CO₂H
|
CH₂—CO₂H,

R₂ represents a member selected from the group consisting of
(i) CH₃,
(ii) —CO₂H,
(iii) —C₆H₅ p—OCH₃,
(iv) —C₆H₅, (v) 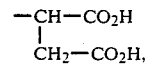

(vi) 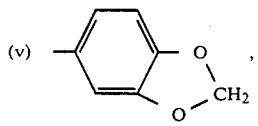

wherein R₄ represents —CH₂COOH or —COCH₃, and (vii) 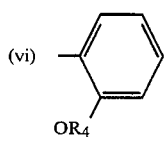

wherein R₅ represents —OH, —OCH₃, —OC₄H₉ or —OCH₂COOH, and

R₃ represents hydrogen or methyl, or R₂ and R₃ together form a divalent radical of the formula —(CH₂)$_m$— or of the formula

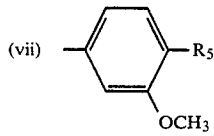

wherein m is 3–5 inclusive and n is 2–5 inclusive and (2) an effective amount of a cosmetic resin.

24. The composition of claim 23 wherein said cosmetic resin is selected from the group consisting of polyvinylpyrrolidone, copolymer of polyvinylpyrrolidone and vinyl acetate, copolymer or vinylacetate and an unsaturated carboxylic acid, copolymer resulting from the polymerization of vinyl acetate, crotonic acid and an acrylic or methacrylic ester, copolymer resulting from the polymerization of vinylacetate, crotonic acid and alkyl vinyl ether and copolymer resulting from the polymerization of vinyl acetate, crotonic acid and an allyl or methallyl ester of a long carbon chain acid.

25. The composition of claim 23 which also includes a liquified gaseous propellant under pressure.

26. The composition of claim 23 wherein said active compound is present in an amount of 0.1 to 10 weight percent thereof and said cosmetic resin is present in an amount of 0.1 to 10 weight percent thereof.

27. The composition of claim 26 wherein said active compound is present in an amount of 1 to 3 weight percent thereof.

28. A cosmetic composition for the treatment of the oily appearance of the hair comprising in combination, in an alcoholic or hydroalcoholic solution, (1) an effective amount of at least one active compound having the formula $$\begin{array}{c} R_2 \diagdown \phantom{C} \diagup S-R_1 \\ C \\ R_3 \diagup \phantom{C} \diagdown S-R_1 \end{array}$$

wherein $R_1$ represents $$\begin{array}{c} -CH-CO_2H \\ | \\ CH_2-CO_2H, \end{array}$$

$R_2$ represents a member selected from the group consisting of (i) $-C_6H_5p-OCH_3$, (ii) $-C_6H_5$, (iii) 2-($OR_4$)-phenyl wherein $R_4$ represents a radical selected from the group consisting of $-CH_2COOH$ and $-COCH_3$, and (iv) 2-($OCH_3$)-phenyl with $R_5$ substituent, wherein $R_5$ represents a radical selected from the group consisting of $-OH$, $-OCH_3$, $-OC_4H_9$ and $-OCH_2COOH$, and $R_3$ represents hydrogen or methyl, or $R_2$ and $R_3$ together form a divalent radical of the formula, phenyl-$(CH_2)_n$ wherein n is 2-5 inclusive, and (2) an effective amount of a cosmetic resin.

* * * * *